United States Patent
Acedo et al.

(10) Patent No.: US 10,610,575 B2
(45) Date of Patent: Apr. 7, 2020

(54) METHOD FOR IMPROVING FEED DIGESTIBILITY IN BOVINE ANIMALS

(71) Applicant: DSM IP ASSETS B.V., Heerlen (NL)

(72) Inventors: Tiago Acedo, Kaiseraugst (CH); Irmgard Immig, Kaiseraugst (CH); Luis Tamassia, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 41 days.

(21) Appl. No.: 15/550,206

(22) PCT Filed: Feb. 12, 2016

(86) PCT No.: PCT/EP2016/052957
§ 371 (c)(1),
(2) Date: Aug. 10, 2017

(87) PCT Pub. No.: WO2016/128530
PCT Pub. Date: Aug. 18, 2016

(65) Prior Publication Data
US 2018/0021415 A1    Jan. 25, 2018

(30) Foreign Application Priority Data

Feb. 12, 2015  (BR) .......................... 1020150032374
Feb. 12, 2015  (EP) .................................... 15154925

(51) Int. Cl.
| | | |
|---|---|---|
| A61K 38/47 | (2006.01) | |
| A61K 31/11 | (2006.01) | |
| A23K 20/189 | (2016.01) | |
| A23K 50/10 | (2016.01) | |
| A23K 20/111 | (2016.01) | |
| A61K 31/085 | (2006.01) | |
| A61K 31/045 | (2006.01) | |
| A61K 31/05 | (2006.01) | |
| A23K 20/195 | (2016.01) | |

(52) U.S. Cl.
CPC ............ *A61K 38/47* (2013.01); *A23K 20/111* (2016.05); *A23K 20/189* (2016.05); *A23K 20/195* (2016.05); *A23K 50/10* (2016.05); *A61K 31/045* (2013.01); *A61K 31/05* (2013.01); *A61K 31/085* (2013.01); *A61K 31/11* (2013.01); *C12Y 302/01001* (2013.01)

(58) Field of Classification Search
CPC ...... A61K 38/47; A61K 31/085; A61K 31/05; A61K 31/045; A61K 31/11; A23K 50/10; A23K 20/189; A23K 20/111; A23K 20/195; C12Y 302/01001
See application file for complete search history.

(56) References Cited

U.S. PATENT DOCUMENTS 8,980,335 B2    3/2015  Frehner et al.

FOREIGN PATENT DOCUMENTS

| EP | 0 897 985 | 2/1999 |
|---|---|---|
| JP | 2014-057591 | 4/2014 |
| WO | WO 95/22625 | 8/1995 |
| WO | WO 96/00343 | 1/1996 |
| WO | WO 99/59430 | 11/1999 |
| WO | WO 01/58275 | 8/2001 |
| WO | WO 03/068256 | 8/2003 |
| WO | WO 2008/092675 | 8/2008 |
| WO | WO 2008/155536 | 12/2008 |

OTHER PUBLICATIONS

International Search Report for PCT/EP2016/052957, dated May 25, 2016, 3 pages.
Tassoul et al., "Essential Oils As Dietary Supplements for Dairy Cows", Nov. 16, 2010, pp. 1-8, XP055203911.
Jouany et al., "Use of 'natural' products as alternatives to antibiotic feed additives in ruminant production", Animal, vol. 1, No. 10, Nov. 2007, 8 pages, XP055019806.
Notice of Reasons for Rejection, JP Appln. No. P2017-538376, dated Nov. 5, 2019.
S.R.Andreazzi, et al., Journal of Dairy Science, vol. 101, No. 8, 2018.
Guilherme G. Silva, et al., Journal of Dairy Science, vol. 101, No. 11, 2018.

*Primary Examiner* — Kade Ariani
(74) *Attorney, Agent, or Firm* — Nixon & Vanderhye P.C.

(57) ABSTRACT

The invention relates to the use of at least one bacterial amylase in combination with a mixture of at least two essential oil compounds selected from the group consisting of thymol, eugenol, meta-cresol, vaniline and guajacol in feed for ruminant animals of the subfamily Bovinae for improving weight gain, milk yield and/or Feed Conversion Ratio (FCR). Examples of bovine animals are beef cattle and dairy cows.

6 Claims, No Drawings

METHOD FOR IMPROVING FEED DIGESTIBILITY IN BOVINE ANIMALS

This application is the U.S. national phase of International Application No. PCT/EP2016/052957 filed 12 Feb. 2016, which designated the U.S. and claims priority to BR Patent Application No. 1020150032374 filed 12 Feb. 2015, and EP Patent Application No. 15154925.0 filed 12 Feb. 2015, the entire contents of each of which are hereby incorporated by reference.

FIELD OF THE INVENTION

High-yielding cows in modern farming systems live under conditions that are characterised by a very high milk production (dairy cows) or growth rate (beef cattle), which is followed by an equally high energy requirement. The utilisation of the feed decreases markedly when intake is increased beyond maintenance levels. In part to account for this, more and more easily degradable feed is included into the ruminant feed e.g. starch-containing raw materials such a cereal-based concentrates and whole cereal silages. The starchy material is frequently recovered in the faeces implying that the utilisation of such feed ingredients could be enhanced further.

The energy content of feed for bovine animals can be measured using an in-vitro fermentation technique developed at the Institute of Animal Nutrition, University of Hohenheim by Prof. Menke and his colleagues in 1979. The Hohenheim feeding value test (HFT) involves the measurement of the volume of gas produced during a 24 hour incubation of animal feed in rumen fluid. The amount of gas produced during the incubation directly correlates with digestibility of the feed and therefore to the energy content. Since the first publication of this method there has been numerous improvements and adaptations made as described by Steingass and Menke, 1986.

Modifications to the HFT allow the changes in the rate of gas production to be observed. Changing certain aspects of the test such as substrate type, substrate preparation and/or incubation time leads to differences in the available energy of the substrate (feed) to the rumen fluid mixture. The adding of certain substances to the HFT fermentation can increase or decrease the digestibility of the substrate. There is, therefore, a need for consistency of procedures such as the equipment and solutions that are used, the taking of measurements and the preparation of the substrate.

In animal feed, maize/corn or maize/corn silage is becoming more common important, in particular in feed for ruminants, due to its efficient growth and for its energy dense properties.

As a consequence of this, improvements in the digestibility of corn and/or starch in ruminant feed need to be made to allow full utilization of the energy potential and all the available nutrients.

A part form that, high-yielding cows that are characterised by a high growth rate (beef cattle) are receiving diets with high concentrate levels of corn. Such diets are widely used for feedlot cattle because they can improve animal performance, carcass characteristics, and consequently increase profitability. Such diets are typically supplemented with Monensin, a carboxylic ionophore originally developed as a poultry coccidiostat. It is known, that Monensin has beneficial growth promoting properties when fed to cattle as it improves feed efficiency and prevents and controls parasite infections in the herd.

The disadvantage of Monensin is that it is a synthetic antibiotic. Thus, there is a continuous need to find a sustainable alternative solution for beef cattle that can reduce the use of antibiotics in animal breeding and farming and that can keep pace with the growing global demand for antibiotic free meat products.

DESCRIPTION OF THE RELATED ART

WO 03/068256 A1 describes an amylase feed supplement for improved ruminant nutrition. The amylase used is a fungal amylase produced by *Aspergillus oryzae*. Tricarico et al, in Animal Science 2005, 81: 365-374, describe the effects of *Aspergillus oryzae* extract containing alpha-amylase activity on ruminal fermentation and milk production in lactating Holstein cows.

Rojo et al (Animal Feed Science and Technology, 123-124 (2005), 655-665) studied the effects of exogenous amylases from *Bacillus licheniformis* and *Aspergillus niger* on ruminal starch digestion and lamb performance.

SUMMARY OF THE INVENTION

It is an object of the present invention to provide an alternative, preferably improved, concept which may alleviate the problems described above by improving feed utilization in feedlot animals, i.e. by improving feed conversion ratio and/or weight gain and by improving milk yield in dairy cows.

It is another object of the present invention to provide an alternative feeding concept for feedlot animals which takes care of a sustainable method for producing animal meat product by replacing all or part of antibiotics in the animal diet.

It has now been found surprisingly that the combined use of a carbohydrase with a mixture of at least two, preferably at least three essential oil compounds selected from the group consisting of thymol, eugenol, meta-cresol, vaniline and guajacol in feed for feedlot animals of the subfamily Bovinae has the advantage of being able to significantly improve digestibility of corn diets.

In particular, the inventors of the present invention have found that the supplementation of a carbohydrase, as for example an amylase, in addition to a mixture of essential oil compounds selected from the group consisting of thymol, eugenol, meta-cresol, vaniline and guajacol improves daily weight gain and feed efficiency in feedlot herds.

Feedlot or feed yard is a type of animal feeding operation which is used in intensive animal farming for finishing livestock, notably beef cattle, but also swine, horses, sheep, turkeys, chickens or ducks, prior to slaughter.

In the present context, an animal of the subfamily Bovinae (also called bovines or bovine animals) means an animal of the kingdom of Animalia, the phylum of Chordata, the class of Mammalia, the order of Artiodactyla, and the family of Bovidae. For the present purposes, domestic cattle are the most preferred species. For the present purposes the term includes all races of domestic cattle, and all production kinds of cattle, in particular beef cattle and dairy cows.

It has been further found that a mixture of at least two, preferably at least three essential oil compounds selected from the group consisting of thymol, eugenol, meta-cresol, vaniline and guajacol in feed for animals of the subfamily Bovinae can be used as an alternative dietary ingredient that can reduce or replace the amount of antibiotics as currently used in the feed for feedlot animals while maintaining the important benefits of said antibiotics.

Therefore, in one embodiment, the invention is related to a method for improving digestibility of diets as used for feedlot animals. More specifically, the invention relates to methods for improving weight gain and/or feed conversion ratio (FCR) of beef cattle in feedlot herds, which comprises providing to the animal an effective amount of at least one carbohydrase in combination with a mixture of at least two, preferably at least three essential oil compounds selected from the group consisting of thymol, eugenol, meta-cresol, vaniline and guajacol.

In another embodiment, the invention concerns a method of sustainably producing an meat product of an animal of the subfamily Bovinae, said method comprising the step of formulating a feed composition which is intended to be used in feedlots by replacing all or part of antibiotic(s) in the composition with a mixture of at least two, preferably at least three essential oil compounds selected from the group consisting of thymol, eugenol, meta-cresol, vaniline and guajacol.

The term feed or feed composition means any compound, preparation, mixture, or composition suitable for, or intended for intake by an animal.

The present invention also relates to a novel feed additive composition for feedlot animals, especially beef cattle, comprising as active ingredient at least one carbohydrase in combination with at least two essential oil compounds as defined above.

DETAILED DESCRIPTION OF THE INVENTION

The essential oil compounds according to the invention are commercially available or can be prepared by a skilled person using processes and methods well-known in the prior art.

The essential oil compounds can be used in highly purified forms in mixtures or in the form of natural available plant extracts or extract-mixtures.

The term "extract" as used herein includes compositions obtained by solvent extraction (which are also known as "extracted oils"), steam distillation (which are also known as "essential oils") or other methods known to the skilled person. Suitable extraction solvents include alcohols such as ethanol.

By the expression "natural" is in this context understood a substance which consists of compounds occurring in nature and obtained from natural products or through synthesis. The natural substance may preferably contain at least two of the compounds as defined above as main ingredient and additionally other essential oil compounds as for example capsaicin, tannin or carvacrol.

With respect to beef cattle, it is at present contemplated that the essential oils are administered in amounts (total dosage ranges of essential oils) of 50 to 150 mg per kg body weight per day, preferably 70 mg to 120 mg per kg body weight per day.

In another preferred embodiment of the invention the essential oils are added to the feed as a single feed additive composition.

The feed additive composition containing the essential oils according to the invention may optionally contain in minor amounts other chemical compounds, for example at least one compound found in plants, and selected from the following group, as, per kg of feed:

up to about 1 mg of propylidene, butylidene, phtalides, gingerol, lavender oil;

up to about 2 mg of deca-, undeca-, dodecalactones, ionones, irone, eucalyptol, menthol, peppermint oil, alpha-pinene;

up to about 3 mg of limonene, anethol, linalool, methyl dihydrojasmonate;

up to about 4 mg of carvacrol, propionic, acetic or butyric acid, rosemary oil, clove oil, geraniol, terpineol, citronellol;

up to about 5 mg of amyl and/or benzyl salicylate, cinnamaldehyde, a plant polyphenol (tannin);

and up to about 5 mg of a powder of turmeric or of an extract of curcuma.

All the essential oils and the additional compounds may be used in combination with an emulsifying surfactant.

The emulsifying agent can be selected advantageously from those of a rather hydrophilic nature, for example among polyglycerol esters of fatty acids such as esterified ricinoleic acid or propylene glycol esters of fatty acids, saccharo-esters or saccharo-glycerides, polyethylene glycol, lecithins etc.

Examples of particularly preferred dosages of the essential oil compounds in a final feed additive composition according to the invention are independently from each other in the following ranges:

thymol between 80 and 120 g/kg, preferably 101 g/kg;
eugenol between 20 and 60 g/kg, preferably 30 g/kg;
meta-cresol 80 and 110 g/kg, preferably 90 g/kg;
vaniline between 30 and 70 g/kg, preferably 50 g/kg
guajacol between 20 and 50 g/kg, preferably 35 g/kg
salicylate between 10 and 30 g/kg, preferably 25 g/kg
resorcine between 5 and 20 g/kg, preferably 15 g/kg In a preferred embodiment of a feeding concept for beef cattle the final feed includes a mixture of thymol, meta-cresol and vaniline, wherein these three compounds being used in amounts sufficient to provide a daily dosage of 50 mg to 150 mg total essential oils per kg body weight of the subject to which it is to be administered.

For purposes of the present invention, a preferred feed additive composition containing the claimed combination of essential oils is available under the commercial product name Crina® Ruminants (available from DSM Nutritional Products AG, Kaiseraugst, Switzerland). Crina® Ruminants is a blend of flavouring compounds for animal nutrition and has content of 380 g/kg total essential oils.

In the present context, a carbohydrase is an enzyme that catalyzes the breakdown of carbohydrates into simple sugars.

Examples of carbohydrases useful in the present context are glucanases, in particular beta-glucanases and xyloglucanases, xylanases, amylases and pectinases and mixtures thereof. In a preferred embodiment of the invention, the carbohydrase is an amylase.

The carbohydrase for use according to the invention is stable in the presence of protease. The protease stability may be determined by incubating 0.5 mg purified carbohydrase enzyme protein/ml in a buffer at a desired pH (e.g. pH 3, 4, or 5), for the desired time (e.g. 30, 45, 60, 90, or 120 minutes) in the presence of protease (e.g. pepsin, 70 mg/l), and then raising pH to the desired pH (e.g. pH 4, 5, 6, or 7) and measuring residual activity. The residual carbohydrase activity is preferably at least 20%, preferably at least 30, 40, 50, 60, 70, 80, or at least 90% relative to the control (a non-protease-treated sample).

In a particular embodiment the at least one carbohydrase is an amylase or an enzyme mixture comprising at least two enzymes selected from the group consisting of beta-glucanases, xyloglucanases, xylanases, amylases and pectinases.

For purposes of the present invention, preferred carbohydrases are the carbohydrases contained in the following commercial products: Ronozyme® RumiStar®, Ronozyme® VP, Ronozyme® WX and Roxazyme® (available from DSM Nutritional Products AG, Kaiseraugst, Switzerland).

In the present context, an amylase is an enzyme that catalyzes the endo-hydrolysis of starch and other linear and branched oligo- and polysaccharides. In a particular embodiment, the amylase for use according to the invention has alpha-amylase activity, viz. catalyzes the endohydrolysis of 1,4-alpha-glucosidic linkages in oligosaccharides and polysaccharides. Alpha-amylases act, e.g., on starch, glycogen and related polysaccharides and oligosaccharides in a random manner, liberating reducing groups in the alpha-configuration.

In a preferred embodiment the amylase of the invention is an alpha-amylase (systematical name: 1,4-alpha-D-glucan glucanohydrolase), preferably a bacterial amylase. In further embodiments, the amylase of the invention belongs to the EC 3.2.1.-group of amylases, such as EC 3.2.1.1 (alpha-amylase), EC 3.2.1.2 (beta-amylase), EC 3.2.1.3 (glucan 1,4-alpha-glucosidase, amyloglucosidase, or glucoamylase), EC 3.2.1.20 (alpha-glucosidase), EC 3.2.1.60 (glucan 1,4-alpha-maltotetraohydrolase), EC 3.2.1.68 (isoamylase), EC 3.2.1.98 (glucan 1,4-alpha-maltohexosidase), or EC 3.2.1.133 (glucan 1,4-alpha-maltohydrolase).

In a preferred embodiment, the amylase for use according to the invention can be, or is, classified as belonging to the EC 3.2.1.1 group. The EC numbers refer to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. the World Wide Web at http://www.chem.gmw.ac.uk/iubmb/enzyme/index.html.

Amylase activity may be determined by any suitable assay. Generally, assay-pH and assay-temperature may be adapted to the enzyme in question. Examples of assay-pH-values are pH 2, 3, 4, 5, 6, 7, 8, 9, 10, 11, or 12. Examples of assay-temperatures are 30, 35, 37, 40, 45, 50, 55, 60, 65, 70, 80, 90, or 95° C. Preferred pH values and temperatures are in the physiological range, such as pH values of 3, 4, 5, 6, 7, or 8, and temperatures of 30, 35, 37, or 40° C. The following amylase assay can be used: Substrate: Phadebas tablets (Pharmacia Diagnostics; cross-linked, insoluble, blue-coloured starch polymer, which is mixed with bovine serum albumin and a buffer substance, and manufactured into tablets). Assay Temperature: 37° C. Assay pH: 4.3 (or 7.0, if desired). Reaction time: 20 min. After suspension in water the starch is hydrolyzed by the alpha-amylase, giving soluble blue fragments. The absorbance of the resulting blue solution, measured at 620 nm, is a function of the alpha-amylase activity. One Fungal alpha-Amylase Unit (1 FAU) is the amount of enzyme which breaks down 5.26 g starch per hour at the standard assay conditions. A preferred starch is Merck, Amylum solubile Erg. B. 6, Batch 9947275. A more detailed assay description, APTSMYQI-3207, is available on request from Novozymes NS, Krogshoejvej 36, DK-2880 Bagsvaerd, Denmark.

For a taxonomical classification and identification of bacteria reference is made to Bergey's Manual of Systematic Bacteriology (1986), vol 2, ISBN0-683-0783. In the alternative, the well-known 16SrRNA sequence analysis can be used (see e.g. Johansen et al, Int. J. Syst. Bacteriol, 1999, 49, 1231-1240, in particular the Methods section on p. 1233, $2^{nd}$ column); or taxonomy experts can be consulted, e.g. from DSMZ or other recognized depositary institutes.

As employed herein the term bacterial designates amylases that are derived from bacteria. The term "derived from" includes enzymes obtainable, or obtained, from wild type bacterial strains, as well as variants thereof. The variants may have at least one substitution, insertion, and/or deletion of at least one amino acid residue. The term variant also includes shufflants, hybrids, chimeric enzymes and consensus enzymes. The variants may have been produced by any method known in the art, such as site-directed mutagenesis, random mutagenesis, consensus derivation processes (EP 897985), and gene shuffling (WO 95/22625, WO 96/00343), etc. For the present purposes an amylase variant qualifies as bacterial when at least one bacterial amylase has been used for its design, derivation or preparation. The term bacterial does not refer to a potential recombinant production host but only to the origin of the amylase encoding gene that is hosted by it.

The amylase for use according to the invention is preferably derived from a strain of *Bacillus*, such as strains of *Bacillus amyloliquefaciens, Bacillus circulans, Bacillus halmapalus, Bacillus licheniformis, Bacillus megaterium, Bacillus* sp., *Bacillus stearothermophilus*, and *Bacillus subtilis*; preferably from strains of *Bacillus amyloliquefaciens, Bacillus halmapalus, Bacillus licheniformis, Bacillus* sp., *Bacillus subtilis*, and *Bacillus stearothermophilus*.

Non-limiting examples of wildtype amylases for use according to the invention are those derived from *Bacillus licheniformis*, such as Swissprot entry name AMY_BACLI, primary accession number P06278; *Bacillus amyloliquefaciens*, such as Swissprot entry name AMY_BACAM, primary accession number P00692; *Bacillus megaterium*, such as Swissprot entry name AMY_BACME, primary accession number P20845; *Bacillus circulans*, such as Swissprot entry name AMY_BACCI, primary accession number P08137; *Bacillus stearothermophilus*, such as Swissprot entry name AMY_BACST, primary accession number P06279. Another example is from *Bacillus subtilis*, such as Swissprot entry name AMY_BACSU, primary accession number P00691.

For purposes of the present invention, preferred amylases are the amylases contained in the following commercial products: BAN, Stainzyme, Termamyl SC, Natalase, and Duramyl (all from Novozymes), and in the Validase BAA and Validase HT products (from Valley Research). Further particular examples of amylases for use according to the invention are the amylases contained in the following commercial products: Clarase, DexLo, GC 262 SP, G-Zyme G990, G-Zyme G995, G-Zyme G997, G-Zyme G998, HTAA, Optimax 7525, Purastar OxAm, Purastar ST, Spezyme AA, Spezyme Alpha, Spezyme BBA, Spezyme Delta AA, Spezyme DBA, Spezyme Ethyl, Spezyme Fred (GC521), Spezyme HPA, and Ultraphlow (all from Genencor); Validase HT340L, Valley Thin 340L (all from Valley Research); Avizyme 1500, Dextro 300 L, Kleistase, Maltazyme, Maxamyl, Thermozyme, Thermatex, Starzyme HT 120 L, Starzyme Super Conc, and Ultraphlo.

In a particular embodiment, the amylase for use according to the invention is pelleting stable, and/or thermostable. The melting temperature (Tm) of an enzyme is a measure of its thermostability. The amylase of the invention may have a Tm of at least 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C. or at least 95° C., as determined by Differential Scanning Calorimetry (DSC). The DSC is performed in a 10 mM sodium phosphate, 50 mM sodium chloride buffer, pH 7.0. The scan rate is constant, e.g. 1.5° C./min. The interval scanned may be from 20 to 100° C. Another buffer may be selected for the scanning, e.g. a buffer of pH 5.0, 5.5, 6.0, or pH 6.5. In further alternative embodiments, a higher or lower scan rate may be used, e.g. a lower one of 1.4° C./min, 1.3° C./min, 1.2° C./min, 1.1° C./min, 1.0° C./min, or 0.9° C./min.

In another preferred embodiment, the amylase for use according to the invention has an activity at pH 7.0 and 37° C. of at least 35% relative to the activity at the pH-optimum and 37° C. More preferably, the activity at pH 7.0 and 37° C. is at least 40, 45, 50, 55, 60, 65, 70, or at least 75% of the activity at the pH-optimum and 37° C.

In another preferred embodiment, the amylase of the invention has an activity at pH 7.0 and 37° C. and in the presence of 5 mM bile salts of at least 25% relative to the activity at the pH-optimum and 37° C. in the absence of bile salts. More preferably, the activity at pH 7.0 and 37° C. and in the presence of 5 mM bile salts is at least 30, 35, 40, 45, 50, 55, 60, or at least 65% of the activity at the pH-optimum and 37° C. in the absence of bile salts.

A bacterial amylase for use according to the present invention is the active enzyme of the commercial product Ronozyme® RumiStar®.

In a particular embodiment, the amylase, in the form in which they are added to the feed, or when being included in a feed additive, are well-defined. Well-defined means, that the enzyme preparation is at least 50% pure on a protein-basis. In other particular embodiments the enzyme preparation is at least 60, 70, 80, 85, 88, 90, 92, 94, or at least 95% pure. Purity may be determined by any method known in the art, e.g. by SDS-PAGE, or by Size-exclusion chromatography (see Example 12 of WO 01/58275).

A well-defined enzyme preparation is advantageous. For instance, it is much easier to dose correctly to the feed an enzyme that is essentially free from interfering or contaminating other enzymes. The term dose correctly refers in particular to the objective of obtaining consistent and constant results, and the capability of optimising dosage based upon the desired effect.

Enzyme preparations with purities of this order of magnitude are in particular obtainable using recombinant methods of production, whereas they are not so easily obtained and also subject to a much higher batch-to-batch variation when produced by traditional fermentation methods.

The bacterial amylase for use according to the invention are included in bovine diets or bovine feed additives in effective amounts. It is presently contemplated that an effective amount is below 200 mg enzyme protein per kg diet dry matter, preferably below 150, 100, 90, 80, 70, 60, 50, 40, 30, 20, 15, 10, 9, 8, or below 7 mg enzyme protein per kg diet dry matter (ppm). On the other hand, an effective amount may be above 0.01 mg enzyme protein per kg diet dry matter, preferably above 0.05, 0.10, 0.15, 0.20, 0.25, 0.30, 0.35, 0.40, 0.45, 0.50, 0.75, 1, 2, 3, or above 4 mg enzyme protein per kg diet dry matter (ppm). Accordingly, non-limiting examples of preferred dose ranges are: 0.10-50 mg enzyme protein/kg, preferably 0.50-10, 1-9, 2-8, 3-8, or 4-7 mg enzyme protein/kg.

In the use according to the invention the mixture of essential oils and the amylase can be fed to the animal before, after, or simultaneously with the diet of the animal. The latter is preferred.

The Feed Conversion Ratio (FCR) is indicative of how effectively a feed is utilized. The FCR may be determined on the basis of an animal growth trial comprising a first treatment in which a mixture of at least two compounds according to the invention in combination with an amylase is added to the animal feed in a suitable concentration per kg feed, and a second treatment (control) with no addition of the compound(s) to the animal feed.

As it is generally known, an improved FCR is lower than the control FCR. In particular embodiments, the FCR is improved (i.e., reduced) as compared to the control by at least 1.0%, preferably at least 1.5%, 1.6%, 1.7%, 1.8%, 1.9%, 2.0%, 2.1%, 2.2%, 2.3%, 2.4%, or at least 2.5%.

An improved weight gain means an improved daily, weekly, bi-weekly, or monthly weight gain (in g or kg per the relevant time period), relative to a control without added amylase and essential oils.

As regards feed compositions for bovines such as beef cattle, the bovine diet is usually composed of an easily degradable fraction (named concentrate) and a fibre-rich less readily degradable fraction which in accordance with the present invention comprises as major part corn. Silage is an ensiled version of the fibre-rich fraction, whereby material with a high water content is treated with a controlled anaerobic fermentation process (naturally-fermented or additive treated).

The feed additive composition of the invention comprises, in addition to the amylase and the essential oils as described hereinabove, at least one additional ingredient selected from amongst vitamins and minerals. For example, the feed additive of the invention may include (i) at least one vitamin, (ii) at least one mineral, or (iii) at least one vitamin and at least one mineral.

The at least one vitamin may be fat-soluble or water-soluble. Examples of fat-soluble vitamins are vitamin A, vitamin D3, vitamin E, and vitamin K, e.g. vitamin K3. Examples of water-soluble vitamins are vitamin B12, biotin and choline, vitamin B1, vitamin B2, vitamin B6, niacin, folic acid and panthothenate, e.g. Ca-D-panthothenate.

The at least one mineral may be a macro minerals and/or a trace mineral. Examples of trace minerals are manganese, zinc, iron, copper, iodine, selenium, and cobalt. Examples of macro minerals are calcium, phosphorus and sodium.

The incorporation of the composition of feed additives as exemplified herein above to animal feeds is in practice carried out using a concentrate or a premix. A premix designates a preferably uniform mixture of one or more micro-ingredients with diluent and/or carrier. Premixes are used to facilitate uniform dispersion of micro-ingredients in a larger mix. A premix according to the invention can be added to feed ingredients or to the drinking water as solids (for example as water soluble powder) or liquids.

A premix may comprise 0.5-10% by weight of the active ingredients according to the invention and 10-95% by weight of other conventional additives, such as flavorings, vitamins, mineral salts and any conventional absorbing support. This premix is finally added to the feed.

The present invention is further described by the following example which should not be construed as limiting the scope of the invention.

EXAMPLE

Effects of Crina® Ruminants and Ronozyme® Rumistar® for Finishing Nelore Cattle in Feedlot Protocol and Design The study has been carried out at facilities of Animal Science Department at ESALQ/USP (University of São Paulo), Piracicaba-SP, Brazil.

Treatments have been allocated in fifty pens, with 6 animals per pen. Water has been supplied for ad libitum consumption and feed once a day. Cattle have been withheld from feed and water for 16 hours before body weight (BW) assessment at the beginning and at the end of the experiment. After 28 and 56 days body weight (BW) has been assessed to monitor the partial average daily gain.

Treatments, Number of Animals and Replicates

| Treatments | |
|---|---|
| 1 | Control: with Monensin |
| 2 | CRINA: Crina Ruminants |
| 3 | Crin + Monensin: Crina Ruminants + Monensin |
| 4 | CriRum: Crina Ruminants + Ronozyme Rumistar |

ANIMALS:

Animal performance trial: 300 finishing bulls, distributed in 50 pens (6 animals per pen).

EXPERIMENTAL DESIGN:

Animal performance trial: randomized blocks, being 6 blocks (10 blocks × 5 treatments)

EXPERIMENTAL MEASUREMENTS AND PROCEDURES:

Complete Feed analysis (diet and ingredients: fed and orts);
Animal performance: Average Daily Gain (ADG)/Dry Matter Intake (DMI)/Feed Efficiency (FE), ADG:DMI Diets: High Concentrate Diets

| INGREDIENTS | FINISHING DIET |
|---|---|
| Corn | 83.00% |
| Sugar cane bagass | 8.50% |
| Soybean meal 45 | 5.50% |
| Urea | 1.00% |
| Mineral | 1.500% |
| Limestone | 0.50% |
| TOTAL | 100.00% |

Results

Results are shown in table 1 and 2.

TABLE 1 adaptation period - 28 days

| | TREATMENTS | | | | | |
|---|---|---|---|---|---|---|
| | 1: MONENSIN | 2: CRINA | 3: M + C | 4: C + R | P value | SEM |
| Initial BW, kg/d | 330.76 | 330.83 | 330.98 | 330.56 | 0.5422 | 10.90 |
| Final BW, kg/d | 382.56b | 388.19a | 382.84b | 391.23a | 0.0053 | 11.07 |
| ADG, kg/d | 1.352b | 1.550a | 1.354b | 1.667a | 0.0054 | 0.084 |
| DMI, kg/d | 7.73b | 8.26a | 7.73b | 8.41a | 0.0163 | 0.31 |
| FE, ADG:DMI | 0.177bc | 0.190ab | 0.177bc | 0.199a | 0.0444 | 0.011 |

M + C = Monensin + Crina,
C + R = Crina + Ronozyme Rumistar,
BW = body weight,
ADG = average daily gain,
DMI = dry matter intake,
FE = feed efficiency Summary: CRINA RUMINANTS increased average daily gain 14.5% and feed efficiency 7.34% in comparison with MONENSIN. CRINA RUMINANTS plus RONOZYME RUMISTAR (Amylase) increased average daily gain 23.3% and feed efficiency 12.4% in comparison with MONENSIN.

TABLE 2

After 59 days

| | 1: MONENSIN | 2: CRINA | 3: M + C | 4: C + R | Pvalue | SEM |
|---|---|---|---|---|---|---|
| Initial BW, kg/d | 330.76 | 330.83 | 330.98 | 330.56 | 0.5422 | 10.90 |
| Final BW, kg/d | 426.72b | 439.05a | 426.40b | 443.62a | 0.0002 | 11.48 |
| ADG, kg/d | 1.342b | 1.540a | 1.334b | 1.622a | 0.0002 | 0.059 |

TABLE 2-continued

| | After 59 days | | | | | |
|---|---|---|---|---|---|---|
| | 1: MONENSIN | 2: CRINA | 3: M + C | 4: C + R | Pvalue | SEM |
| DMI, kg/d | 8.63b | 9.23a | 8.58b | 9.42a | 0.0003 | 0.28 |
| FE, ADG:DMI | 0.155b | 0.167ab | 0.156b | 0.172a | 0.0686 | 0.008 |

M + C = Monensin + Crina,
C + R = Crina + Ronozyme Rumistar

Summary: CRINA RUMINANTS increased average daily gain 14.7% and feed efficiency 7.75% in comparison with MONENSIN. CRINA RUMINANTS plus RONOZYME RUMISTAR (Amylase) increased average daily gain 20.8% and feed efficiency 10.9% in comparison with MONENSIN.

The invention claimed is:

1. A method of improving weight gain and/or feed conversion ratio of animals of the subfamily Bovinae, wherein the method comprises administering to the animal a feed additive composition comprising as active at least one amylase in combination with a mixture of at least two essential oil compounds selected from the group consisting of thymol, eugenol, meta-cresol, vanillin and guaiacol, thereby improving weight gain and/or feed conversion ratio of said animal.

2. The method according to claim 1, wherein the at least two essential oil compounds are administered in a total amount of the essential oils of 50 to 150 mg per kg body weight per day.

3. The method according to claim 1, wherein the animal is a domestic cattle.

4. The method according to claim 1, wherein the animal is a dairy cow.

5. The method according to claim 1, wherein the animal is a beef cattle.

6. The method according to claim 1, wherein the essential oils are administers in a total amount of 70 mg to 120 mg per kg body weight per day.

* * * * *